United States Patent
Han et al.

(10) Patent No.: US 11,787,695 B1
(45) Date of Patent: Oct. 17, 2023

(54) CARBON NEUTRAL CONVERSION OF RESIDUE

(71) Applicant: Saudi Arabian Oil Company, Dhahran (SA)

(72) Inventors: Chun Han, Dhahran (SA); Salahdine Idrissi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/974,259

(22) Filed: Oct. 26, 2022

(51) Int. Cl.
| | |
|---|---|
| C01B 3/36 | (2006.01) |
| B01J 19/24 | (2006.01) |
| C07C 29/151 | (2006.01) |
| C07C 1/24 | (2006.01) |
| C07C 51/12 | (2006.01) |
| C10K 3/04 | (2006.01) |
| C10K 1/00 | (2006.01) |
| B01D 53/14 | (2006.01) |
| B01D 53/047 | (2006.01) |

(Continued)

(52) U.S. Cl.
CPC ............. *C01B 3/36* (2013.01); *B01D 53/047* (2013.01); *B01D 53/1462* (2013.01); *B01D 53/229* (2013.01); *B01J 19/245* (2013.01); *B01J 19/2445* (2013.01); *C01B 3/12* (2013.01); *C07C 1/24* (2013.01); *C07C 29/1518* (2013.01); *C07C 51/12* (2013.01); *C10K 1/004* (2013.01); *C10K 3/04* (2013.01); *B01D 2257/304* (2013.01); *B01D 2257/502* (2013.01); *B01D 2257/504* (2013.01); *C01B 2203/0283* (2013.01); *C01B 2203/047* (2013.01); *C01B 2203/0475* (2013.01); *C01B 2203/061* (2013.01)

(58) Field of Classification Search
CPC ....... C07C 51/12; C07C 1/24; C07C 29/1518; C01B 2203/61; C01B 2203/0283; C01B 2203/047; C01B 2203/0475; C01B 3/36; C01B 3/12
See application file for complete search history.

(56) References Cited

U.S. PATENT DOCUMENTS 6,596,781 B1 * 7/2003 Schinski ................. C07C 51/12
518/703

FOREIGN PATENT DOCUMENTS

| CA | 2800166 | 11/2010 |
|---|---|---|
| EP | 3878807 | 9/2021 |

OTHER PUBLICATIONS

Audus, "Leading Options for the Capture of CO2 at Power Stations," IEA Greenhouse Gas R&D Programme, UK, 2000, 6 pages.

(Continued)

*Primary Examiner* — Jafar F Parsa
(74) *Attorney, Agent, or Firm* — Fish & Richardson P.C.

(57) ABSTRACT

A petroleum residue stream is heated and reacted with an oxygen stream and a carbon dioxide stream in a gasification unit to produce syngas. At least a portion of the carbon monoxide is converted into carbon dioxide to produce shifted syngas. At least a portion of the shifted syngas is separated to produce a syngas feed stream. At least a portion of the syngas feed stream is converted into methanol. At least a portion of the methanol is converted into one or more alkenes (olefins). At least a portion of the methanol is reacted with carbon monoxide to produce acetic acid. Carbon dioxide produced in the process can be recycled to the gasification unit to facilitate the production of the syngas.

12 Claims, 2 Drawing Sheets

(51) Int. Cl.
*B01D 53/22* (2006.01)
*C01B 3/12* (2006.01)

(56) References Cited

OTHER PUBLICATIONS

Jones, "The Cativa™ Process for the Manufacture of Acetic Acid," Platinum Metals Rev, 2000, 44(3):94-105, 12 pages.
O'Keefe et al., "A Single IGCC Design for Variable CO2 Capture," General Electric Power Systems, 2002, 10 pages.
Tian et al., "Methanol to Olefins (MTO): From Fundamentals to Commercialization," ACS Catalysis, 2015, 5:1922-1938, 17 pages.
Yang et al., "Biomass-to-Methanol by dual-stage entrained flow gasification: Design and techno-economic analysis based on system modeling," Journal of Cleaner Production, 2018, 37 pages.
Zdeb et al., "Utilization of Carbon Dioxide in Coal Gasification—An Experimental Study," Energies, 2019, 12(140), 12 pages.

* cited by examiner

CARBON NEUTRAL CONVERSION OF RESIDUE

TECHNICAL FIELD

This disclosure relates to conversion of petroleum residue into chemical products.

BACKGROUND

Residuum produced in refineries are sometimes used to produce refinery fuel oil, for example, by blending with cutter stock (typically distillate or heavy gas oil) to produce transportable and marketable fuel oil. Some refineries utilize thermal cracking technology to improve the economic value of their product yields and to improve the viscosity of the straight run residual that is produced from crude oil. Fuel oil produced by such operations are also known as cracked fuel oil. Cracked fuel oil and blends that include cracked fuel oil are typically limited to use as low value fuel, for example, as marine bunker fuel, power plant fuel, or industrial utility fuel.

SUMMARY

This disclosure describes technologies relating to carbon neutral processes and systems for converting petroleum residue into chemicals and commodity products. Certain aspects of the subject matter can be implemented as a method. A petroleum residue stream is heated and reacted with an oxygen stream and a carbon dioxide stream in a gasification unit to produce a syngas stream. The carbon dioxide stream entering the gasification unit can be a recycled carbon dioxide stream (for example, a carbon dioxide stream produced in the process and recycled back to the gasification unit). The syngas stream from the gasification unit includes raw syngas that includes carbon monoxide, hydrogen, and carbon dioxide. In some cases, the syngas stream from the gasification unit includes impurities. The syngas stream from the gasification unit (raw syngas) can be processed (for example, cooled and scrubbed) prior to being sent to a water-gas shift unit. At least a portion of the carbon monoxide of the syngas stream from the gasification unit is converted (for example, in a water-gas shift reactor) into carbon dioxide to produce a shifted syngas stream. The shifted syngas stream can be sent to an acid gas removal unit for removal of sulfur-containing compounds (such as $H_2S$ and COS) and partitioning of the sulfur-free (clean) syngas into various streams for downstream conversion processes. At least a portion of the shifted syngas stream is separated to produce a syngas feed stream. Separating at least the portion of the shifted syngas stream includes separating at least a portion of carbon dioxide from the shifted syngas stream to produce a recycle carbon dioxide stream. Separating at least the portion of the shifted syngas stream includes separating at least a portion of carbon monoxide from the shifted syngas stream to produce a carbon monoxide stream. At least a portion of the syngas feed stream are converted into methanol to produce a methanol stream. At least a first portion of the methanol stream is converted into one or more alkenes to produce an olefins stream. At least a second portion of (for example, a remainder of) the methanol stream is reacted with at least a portion of (for example, all of) the carbon monoxide stream to produce acetic acid. At least a portion of (for example, all of) the recycle carbon dioxide stream is recycled to the gasification unit to facilitate the production of the syngas stream. Process parameters (such as operating pressures, operating temperatures, and flow rates) can be optimized to convert all of the carbon in the feedstock (petroleum residue stream) into the final products to achieve carbon-neutral conversion of the petroleum residue.

This, and other aspects, can include one or more of the following features. In some implementations, the petroleum residue stream includes residue from an atmospheric distillation column, residue from a vacuum distillation column, residue from a visbreaker, fuel oil, pitch from solvent deasphalting, or any combination of these. In some implementations, the petroleum residue stream is heated and reacted with the oxygen stream and the carbon dioxide stream in the gasification unit at a gasification operating pressure in a range of from about 4,000 kilopascals (kPa) to about 8,500 kPa and a gasification operating temperature in a range of from about 900 degrees Celsius (° C.) to about 1100° C. In some implementations, steam is injected into the gasification unit to control the gasification operating temperature. In some implementations, a mass ratio of the petroleum residue stream to the oxygen stream entering the gasification unit is in a range of from about 1.2 to about 1.5. In some implementations, a volume ratio of hydrogen to carbon monoxide in the shifted syngas stream is in a range of from about 0.7 to about 1.0. In some implementations, the portion of carbon dioxide and the portion of carbon monoxide of the syngas feed stream is converted into methanol at a methanol synthesis operating pressure in a range of from about 5,000 kPa to about 12,000 kPa and a methanol synthesis operating temperature in a range of from about 200° C. to about 300° C. In some implementations, a mass ratio of the methanol stream to the petroleum residue stream is in a range of from about 0.9 to about 1.2. In some implementations, the portion of the methanol stream is reacted with the portion of the carbon monoxide stream to produce acetic acid at an acetic acid synthesis operating pressure in a range of from about 3,000 kPa to about 6,000 kPa and an acetic acid synthesis operating temperature in a range of from about 150° C. to about 200° C. In some implementations, a mass ratio of the acetic acid to the petroleum residue stream is in a range of from about 1.2 to about 1.7. In some implementations, a mass ratio of the portion of the carbon monoxide stream that is reacted with the second portion of the methanol stream to the petroleum residue stream is in a range of from about 0.5 to about 0.8. In some implementations, the olefins stream comprises ethylene and propylene, and a ratio of ethylene to propylene in the olefins stream is in a range of from about 0.6 to about 1.3. In some implementations, a mass ratio of the olefins stream to the petroleum residue stream is in a range of from about 0.01 to about 0.03.

Certain aspects of the subject matter described can be implemented as a system. The system includes a gasification unit, a water-gas shift unit, an acid gas removal unit, a methanol synthesis unit, a methanol-to-olefins unit, an acetic acid production unit, and a carbon dioxide compression unit. The gasification unit is configured to receive a petroleum residue stream, an oxygen stream, and a carbon dioxide stream. The gasification unit is configured to react the petroleum residue stream with the oxygen stream and the carbon dioxide stream to produce a syngas stream. The syngas stream includes carbon dioxide, carbon monoxide, and hydrogen. The water-gas shift unit is configured to receive the syngas stream from the gasification unit. The water-gas shift unit is configured to convert at least a portion of the carbon monoxide of the syngas stream into carbon dioxide to produce a shifted syngas stream. The acid gas removal unit is configured to receive the shifted syngas stream from the water-gas shift unit. The acid gas removal unit is configured to separate at least a portion of carbon dioxide from the shifted syngas stream to produce a recycle carbon dioxide stream and separate at least a portion of carbon monoxide from the shifted syngas stream to produce a carbon monoxide stream and a syngas feed stream. The methanol synthesis unit is configured to receive the syngas feed stream from the acid gas removal unit. The methanol synthesis unit is configured to convert at least a portion of carbon dioxide and at least a portion of carbon monoxide of the syngas feed stream into methanol to produce a methanol stream. The methanol-to-olefins unit is configured to receive at least a first portion of the methanol stream from the methanol synthesis unit. The methanol-to-olefins unit is configured to convert at least the first portion of the methanol stream into one or more alkenes to produce an olefins stream. The acetic acid production unit is configured to receive at least a second portion of the methanol stream from the methanol synthesis unit and at least a portion of the carbon monoxide stream from the acid gas removal unit. The acetic acid production unit is configured to react at least the second portion of the methanol stream with at least the portion of the carbon monoxide stream to produce acetic acid. The carbon dioxide compression unit is configured to receive at least a portion of the recycle carbon dioxide stream from the acid gas removal unit. The carbon dioxide compression unit is configured to pressurize at least the portion of the recycle carbon dioxide stream and recycle the pressurized portion of the recycle carbon dioxide stream to the gasification unit to facilitate production of the syngas stream.

This, and other aspects, can include one or more of the following features. In some implementations, the system includes the petroleum residue stream. In some implementations, the petroleum residue stream includes residue from an atmospheric distillation column, residue from a vacuum distillation column, residue from a visbreaker, fuel oil, pitch from solvent deasphalting, or any combination of these. In some implementations, the system includes the oxygen stream. In some implementations, a mass ratio of the petroleum residue stream to the oxygen stream entering the gasification unit is in a range of from about 1.2 to about 1.5. In some implementations, the system includes the shifted syngas stream. In some implementations, a volume ratio of hydrogen to carbon monoxide in the shifted syngas stream is in a range of from about 0.7 to about 1.0. In some implementations, the system includes the methanol stream. In some implementations, a mass ratio of the methanol stream to the petroleum residue stream is in a range of from about 0.9 to about 1.2. In some implementations, the system includes the acetic acid. In some implementations, a mass ratio of the acetic acid to the petroleum residue stream is in a range of from about 1.2 to about 1.7. In some implementations, the system includes the carbon monoxide stream. In some implementations, a mass ratio of the portion of the carbon monoxide stream that is reacted with the portion of the methanol stream to the petroleum residue stream is in a range of from about 0.5 to about 0.8. In some implementations, the system includes the olefins stream. In some implementations, a mass ratio of the olefins stream to the petroleum residue stream is in a range of from about 0.01 to about 0.03.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes a process for converting petroleum residue into chemicals, such as methanol, olefins, polyethylene, polypropylene, carbon monoxide, and acetic acid. The process includes gasification of the petroleum residue to produce syngas. The syngas is processed to produce methanol and separate a carbon dioxide stream and a carbon monoxide stream. At least a portion of the methanol can be processed to produce olefins (alkenes). At least a portion of the methanol can be reacted with the carbon monoxide stream to produce acetic acid. At least a portion of the carbon dioxide stream is recycled to the gasification unit to improve overall efficiency of the process and reduce emissions.

The subject matter described in this disclosure can be implemented in particular implementations, so as to realize one or more of the following advantages. The processes and systems described can be used to convert residuum from crude oil processing (which is considered of low value) into more valuable chemical products, such as methanol, olefins, polyethylene, polypropylene, and acetic acid. The processes and systems described can be implemented as carbon neutral processes that mitigate and/or eliminate emissions associated with processing of crude oil residuum. The processes and systems described can be implemented to reduce consumption of oxygen, which can reduce costs associated with air separation. The processes and systems described can be implemented to increase the on-stream factor (and therefore reduce costs) for consumable elements of the gasifier, such as refractory elements and feed injectors because of the reduced gasification temperature.

Figure 1:
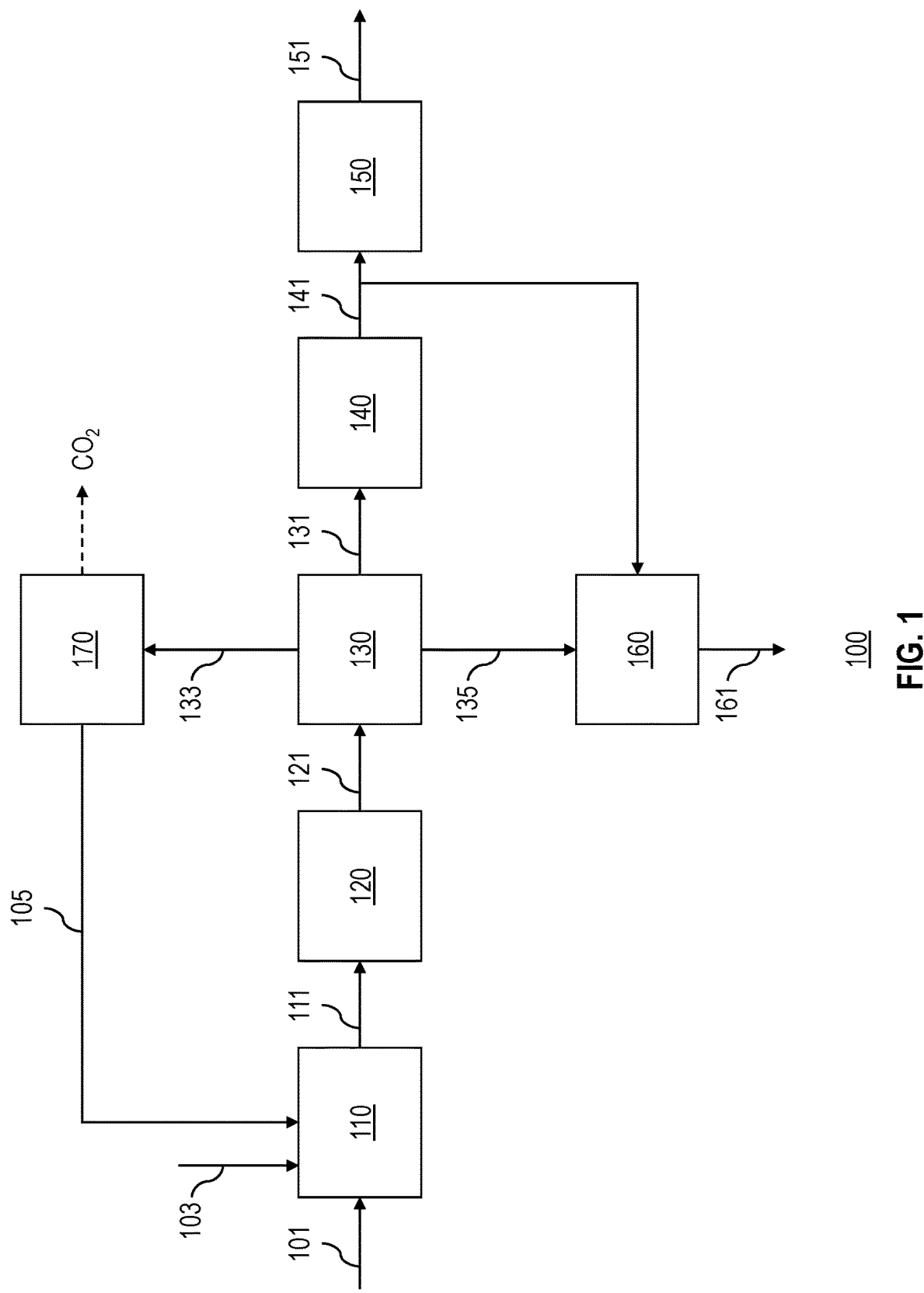
FIG. 1 is a schematic diagram of an example system for converting petroleum residue into chemical products.

FIG. 1 depicts an example system 100 for converting petroleum residue into chemicals, such as methanol, olefins, polyethylene, polypropylene, carbon monoxide, and acetic acid. The system 100 includes a gasification unit 110, a water-gas shift unit 120, an acid gas removal unit 130, a methanol synthesis unit 140, a methanol-to-olefins unit 150, an acetic acid production unit 160, and a carbon dioxide compression unit 170. In some implementations, the system 100 includes a petroleum residue stream 101, an oxygen stream 103, a carbon dioxide stream 105, a syngas stream 111, a shifted syngas stream 121, a syngas feed stream 131, a recycle carbon dioxide stream 133, a carbon monoxide stream 135, a methanol stream 141, an olefins stream 151, and an acetic acid stream 161. The petroleum residue stream 101 includes residue from processing of crude oil. For example, the petroleum residue stream 101 includes residue from an atmospheric distillation column, residue from a vacuum distillation column, residue from a visbreaker, fuel oil, pitch from solvent deasphalting, or any combination of these.

The gasification unit 110 is configured to receive the petroleum residue stream 101, the oxygen stream 103, and the carbon dioxide stream 105. The gasification unit 110 is configured to react the petroleum residue stream 101 with the oxygen stream 103 and the carbon dioxide stream 105 to produce the syngas stream 131. For example, the gasification unit 110 includes a gasifier that includes a burner (feed injector) for introducing feeds to the gasification process. The syngas stream 111 includes carbon dioxide, carbon monoxide, and hydrogen. As one example, a relative molar ratio of hydrogen to carbon monoxide to carbon dioxide in the syngas stream 111 can be 42:53:3. In some cases, the syngas stream 111 includes one or more contaminants, such as hydrogen sulfide ($H_2S$), hydrogen cyanide (HCN), and carbonyl sulfide (OCS). In some implementations, the gasification unit 110 is configured to heat and react the petroleum residue stream 101 with the oxygen stream 103 and the carbon dioxide stream 105 to produce the syngas stream 131 at a gasification operating pressure in a range of from about 4,000 kilopascals (kPa) to about 8,500 kPa and a gasification operating temperature in a range of from about 900 degrees Celsius (° C.) to about 1100° C. In some implementations, steam is injected into the gasification unit 110 to control/regulate the gasification operating temperature to be in the range of from about 900° C. to about 1100° C. In some implementations, a mass ratio of the petroleum residue stream 101 to the oxygen stream 103 entering the gasification unit 110 is in a range of from about 1.2 to about 1.5 or from about 1.3 to about 1.4.

The water-gas shift unit 120 is configured to receive the syngas stream 111 from the gasification unit 110. The water-gas shift unit 120 is configured to convert at least a portion of the carbon monoxide of the syngas stream 111 into carbon dioxide to produce a shifted syngas stream 121. For example, the water-gas shift unit 120 includes a reactor and a water-gas shift catalyst that increases the rate of conversion of carbon monoxide into carbon dioxide for producing the shifted syngas stream 121. The extent of carbon monoxide conversion to carbon dioxide (shift) in the water-gas shift unit 120 can be adjusted (for example, by adjusting process parameters), depending on the desired downstream product slates/specifications. In some implementations, a volume (or molar) ratio of hydrogen to carbon monoxide in the shifted syngas stream 121 is in a range of from about 0.7 to about 1.0 or from about 0.8 to about 0.9. As one example, a relative molar ratio of hydrogen to carbon monoxide to carbon dioxide in the shifted syngas stream 121 can be 45:50:5 on a dry basis. In some implementations, the water-gas shift unit 120 is configured to cool the syngas stream 111 received from the gasification unit 110. The degree of cooling of the syngas stream 111 can be adjusted based on the water-gas shift catalyst requirements. The water-gas shift catalyst can include alkali oxides, such as a bimetallic cobalt-molybdenum (Co—Mo) catalyst supported by aluminum oxide ($Al_2O_3$) for enhanced water capturing ability. For example, the water-gas shift catalyst includes from about 5% to about 10% molybdenum, up to about 5% cobalt, from about 1% to about 25% alkali metals (such as sodium, potassium, calcium, or magnesium) with the balance of aluminum oxide ($Al_2O_3$).

The acid gas removal (AGR) unit 130 is configured to receive the shifted syngas stream 121 from the water-gas shift unit 120. The acid gas removal unit 130 can be configured to process the shifted syngas stream 121 for multiple purposes. The acid gas removal unit 130 is configured to separate at least a portion of carbon dioxide from the shifted syngas stream 121 to produce the recycle carbon dioxide stream 133. The acid gas removal unit 130 is configured to separate at least a portion of carbon monoxide from the shifted syngas stream 121 to produce the carbon monoxide stream 135. The acid gas removal unit 130 can also be configured to remove sulfur-containing compounds (such as $H_2S$ and COS) from the shifted syngas stream 121. The acid gas removal unit 130 produces a syngas feed stream 131 that has been "cleaned". The syngas feed stream 131 includes the remaining components from the shifted syngas stream 121 after the carbon dioxide, carbon monoxide, and contaminants (for example, other acid gases, such as $H_2S$, HCN, and COS) have been removed. For example, the acid gas removal unit 130 includes a solvent absorber column (for selective absorption of $H_2S$ and $CO_2$), combined membrane and pressure swing adsorption (for separation of carbon monoxide and hydrogen gas), and solvent regeneration for removing acid gases from the shifted syngas stream 121 to produce the syngas feed stream 131. In some implementations, the integration of the water-gas shift unit 120, the acid gas removal unit 130, and pressure swing adsorption (PSA) can generate a high purity carbon dioxide stream, a high purity carbon monoxide stream, and a high purity hydrogen stream to meet downstream product requirements.

The methanol synthesis unit 140 is configured to receive the syngas feed stream 131 from the acid gas removal unit 130. The methanol synthesis unit 140 is configured to convert at least a portion of the syngas feed stream 131 into methanol to produce the methanol stream 141. For example, the methanol synthesis unit 140 includes a catalytic reactor to convert the syngas feed stream 131 into methanol for producing the methanol stream 141. In some implementations, the methanol synthesis catalyst includes copper, zinc, chromium, or any combination of these. In some implementations, the methanol synthesis unit 140 is configured to synthesize methanol at a methanol synthesis operating pressure in a range of from about 5,000 kPa to about 12,000 kPa and a methanol synthesis operating temperature in a range of from about 200° C. to about 300° C. In some implementations, a mass ratio of the methanol stream 141 to the petroleum residue stream 101 (feed) is in a range of from about 0.9 to about 1.2 or from about 1.0 to about 1.1.

The methanol-to-olefins unit 150 is configured to receive at least a first portion of the methanol stream 141 from the methanol synthesis unit 140. The methanol-to-olefins unit 150 is configured to convert at least the first portion of the methanol stream 141 into one or more alkenes (such as ethylene and propylene) to produce the olefins stream 151. For example, the methanol-to-olefins unit 150 includes a catalytic reactor to convert methanol into alkenes for producing the olefins stream 151. In some implementations, the olefins stream 151 includes ethylene and propylene. In some implementations, a molar ratio of ethylene to propylene in the olefins stream 151 is in a range of from about 0.6 to about 1.3 or from about 0.7 to about 1.2. In some implementations, a mass ratio of the olefins stream 151 to the petroleum residue stream 101 (feed) is in a range of from about 0.01 to about 0.03.

The acetic acid production unit 160 is configured to receive at least a second portion of the methanol stream 141 from the methanol synthesis unit 140 and at least a portion of the carbon monoxide stream 135 from the acid gas removal unit 130. The acetic acid production unit 160 is configured to react at least the second portion of the methanol stream 141 with at least the portion of the carbon monoxide stream 135 to produce acetic acid (acetic acid stream 161). For example, the acetic acid production unit 160 includes a catalytic reactor to convert methanol and carbon monoxide into acetic acid for producing the acetic acid stream 161. In some implementations, the acetic acid production unit 160 utilizes a rhodium-based catalyst. In some implementations, the acetic acid production unit 160 is configured to synthesize acetic acid at an acetic acid synthesis operating pressure in a range of from about 3,000 kPa to about 6,000 kPa and an acetic acid synthesis operating temperature in a range of from about 150° C. to about 200° C. In some implementations, a mass ratio of the acetic acid stream 161 to the petroleum residue stream 101 (feed) is in a range of from about 1.2 to about 1.7 or from about 1.3 to about 1.6. In some implementations, a mass ratio of (A) the portion of the carbon monoxide stream 135 that is reacted with the second portion of the methanol stream 141 to (B) the petroleum residue stream 101 (feed) is in a range of from about 0.5 to about 0.8 or from about 0.6 to about 0.7.

The carbon dioxide compression unit 170 is configured to receive at least a portion of the recycle carbon dioxide stream 133 from the acid gas removal unit 130. The carbon dioxide compression unit 170 is configured to pressurize at least the portion of the recycle carbon dioxide stream 133 to produce a pressurized recycle carbon dioxide stream which is recycled as the carbon dioxide stream 105 to the gasification unit 110. For example, the carbon dioxide compression unit 170 includes a compressor that pressurizes at least the portion of the recycle carbon dioxide stream 133 for producing the pressurized recycle carbon dioxide stream (105). In some implementations, the compressor is configured to pressurize at least the portion of the recycle carbon dioxide stream 133, such that the pressurized recycle carbon dioxide stream (105) discharged from the compressor has an operating pressure in a range of from about 6,000 kPa to about 8,500 kPa. The discharge pressure of the compressor can be adjusted to meet the operating conditions of the gasification unit 110. The carbon dioxide compression unit 170 is configured to recycle the pressurized recycle carbon dioxide stream (105) to the gasification unit 110 to facilitate production of the syngas stream 111. As one example, the carbon dioxide compression unit 170 can be configured to recycle about 7.5 to about 8.5 million standard cubic feet per day (MMSCFD) of carbon dioxide (105) on a basis of about 2,000 metric tonnes per day (MTPD) of petroleum residue (101) entering the gasification unit 110.

Figure 2:
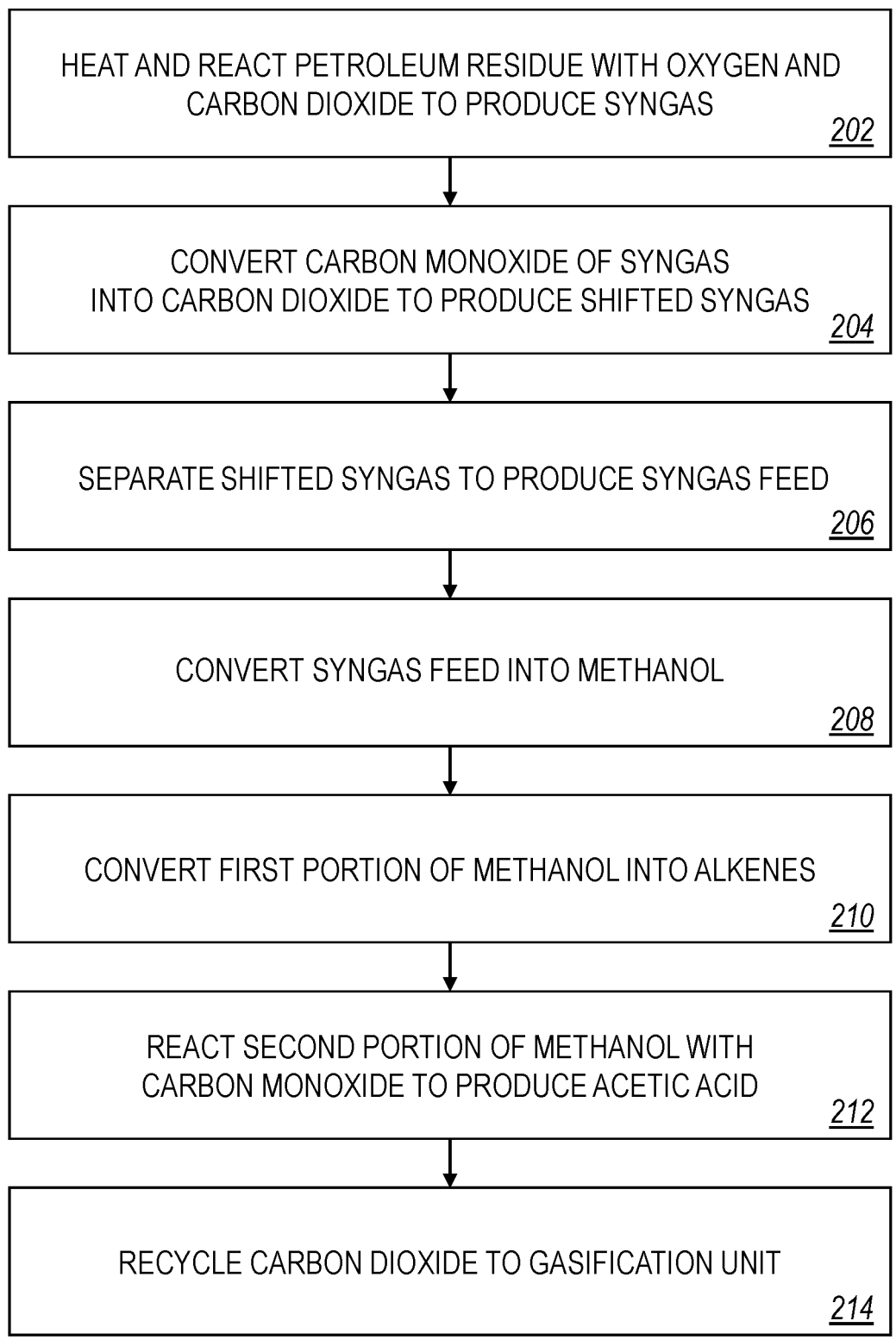
FIG. 2 is a flow chart of an example method for converting petroleum residue into chemical products.

FIG. 2 is a flow chart of an example method 200 for converting petroleum residue into chemicals, such as methanol, olefins, polyethylene, polypropylene, carbon monoxide, and acetic acid. As an example, the system 100 can be used to implement the method 200. At block 202, a petroleum residue stream (such as the petroleum residue stream 101) is heated and reacted with an oxygen stream (such as the oxygen stream 103) and a carbon dioxide stream (such as the carbon dioxide stream 105) in a gasification unit (such as the gasification unit 110) to produce a syngas stream (such as the syngas stream 111). As described previously, the syngas stream 111 includes a mixture of carbon dioxide, carbon monoxide, and hydrogen. The gasification unit 110 can, for example, perform block 202. At block 204, at least a portion of the carbon monoxide of the syngas stream 111 is converted into carbon dioxide to produce a shifted syngas stream (such as the shifted syngas stream 121). The water-gas shift unit 120 can, for example, perform block 204. At block 206, at least a portion of the shifted syngas stream 121 the shifted syngas stream 121 to produce a syngas feed stream 131. The acid gas removal unit 130 can, for example, perform block 206. For example, acid gas components (such as $H_2S$, HCN, and COS) are removed from the shifted syngas stream 121 at block 206. Separating the shifted syngas stream 121 at block 206 includes separating at least a portion of carbon dioxide from the shifted syngas stream 121 to produce a recycle carbon dioxide stream (such as the recycle carbon dioxide stream 133). Separating the shifted syngas stream 121 at block 206 includes separating at least a portion of carbon monoxide from the shifted syngas stream 121 to produce a carbon monoxide stream (such as the carbon monoxide stream 135). At block 208, at least a portion of the syngas feed stream 131 is converted into methanol to produce a methanol stream (such as the methanol stream 141). The methanol synthesis unit 140 can, for example, perform block 208. At block 210, at least a first portion of the methanol stream 141 is converted into one or more alkenes (for example, ethylene, propylene, butylene, and butadiene) to produce an olefins stream (such as the olefins stream 151). The methanol-to-olefins unit 150 can, for example, perform block 210. At block 212, at least a second portion of the methanol stream 141 is reacted with at least a portion of the carbon monoxide stream 135 to produce acetic acid. The acetic acid production unit 160 can, for example, perform block 212. The acetic acid produced at block 212 can, for example, be discharged by the acetic acid production unit 160 as the acetic acid stream 161. At block 214, at least a portion of the recycle carbon dioxide stream 133 is recycled to the gasification unit 110 to facilitate the production of the syngas stream 111 (block 202). Recycling at least the portion of the recycle carbon dioxide stream 133 at block 214 can include pressurizing the recycle carbon dioxide stream 133 to form a pressurized recycle carbon dioxide stream (such as the pressurized recycle carbon dioxide stream 105) and flowing the pressurized recycle carbon dioxide stream 105 to the gasification unit 110. The carbon dioxide compression unit 170 can, for example, perform block 214.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A method comprising:
   heating and reacting a petroleum residue stream with an oxygen stream and a carbon dioxide stream in a gasification unit to produce a syngas stream comprising carbon dioxide, carbon monoxide, and hydrogen;
   converting at least a portion of the carbon monoxide of the syngas stream into carbon dioxide to produce a shifted syngas stream;
   separating at least a portion of the shifted syngas stream to produce a syngas feed stream, wherein separating at least the portion of the shifted syngas stream comprises:
      separating at least a portion of carbon dioxide from the shifted syngas stream to produce a recycle carbon dioxide stream; and
      separating at least a portion of carbon monoxide from the shifted syngas stream to produce a carbon monoxide stream;
   converting at least a portion of the syngas feed stream into methanol to produce a methanol stream;
   converting at least a first portion of the methanol stream into one or more alkenes to produce an olefins stream;
   reacting at least a second portion of the methanol stream with at least a portion of the carbon monoxide stream to produce acetic acid; and
   recycling at least a portion of the recycle carbon dioxide stream to the gasification unit to facilitate the production of the syngas stream.

2. The method of claim 1, wherein the petroleum residue stream comprises residue from an atmospheric distillation column, residue from a vacuum distillation column, residue from a visbreaker, fuel oil, pitch from solvent deasphalting, or any combination thereof.

3. The method of claim 2, wherein the petroleum residue stream is heated and reacted with the oxygen stream and the carbon dioxide stream in the gasification unit at a gasification operating pressure in a range of from about 4,000 kilopascals (kPa) to about 8,500 kPa and a gasification operating temperature in a range of from about 900 degrees Celsius (° C.) to about 1100° C.

4. The method of claim 3, wherein a mass ratio of the petroleum residue stream to the oxygen stream entering the gasification unit is in a range of from about 1.2 to about 1.5.

5. The method of claim 4, wherein a volume ratio of hydrogen to carbon monoxide in the shifted syngas stream is in a range of from about 0.7 to about 1.0.

6. The method of claim 5, wherein the portion of carbon dioxide and the portion of carbon monoxide of the syngas feed stream is converted into methanol at a methanol synthesis operating pressure in a range of from about 5,000 kPa to about 12,000 kPa and a methanol synthesis operating temperature in a range of from about 200° C. to about 300° C.

7. The method of claim 6, wherein a mass ratio of the methanol stream to the petroleum residue stream is in a range of from about 0.9 to about 1.2.

8. The method of claim 7, wherein the portion of the methanol stream is reacted with the portion of the carbon monoxide stream to produce acetic acid at an acetic acid synthesis operating pressure in a range of from about 3,000 kPa to about 6,000 kPa and an acetic acid synthesis operating temperature in a range of from about 150° C. to about 200° C.

9. The method of claim 8, wherein a mass ratio of the acetic acid to the petroleum residue stream is in a range of from about 1.2 to about 1.7.

10. The method of claim 9, wherein a mass ratio of the portion of the carbon monoxide stream that is reacted with the second portion of the methanol stream to the petroleum residue stream is in a range of from about 0.5 to about 0.8.

11. The method of claim 10, wherein the olefins stream comprises ethylene and propylene, and a ratio of ethylene to propylene in the olefins stream is in a range of from about 0.6 to about 1.3.

12. The method of claim 11, wherein a mass ratio of the olefins stream to the petroleum residue stream is in a range of from about 0.01 to about 0.03.

* * * * *